United States Patent [19]
Tsai et al.

[11] Patent Number: 4,845,558
[45] Date of Patent: Jul. 4, 1989

[54] METHOD AND APPARATUS FOR DETECTING DEFECTS IN REPEATED MICROMINIATURE PATTERNS

[75] Inventors: Bin-ming B. Tsai, Santa Clara; Fred E. Babian, Boulder Creek, both of Calif.

[73] Assignee: KLA Instruments Corporation, Santa Clara, Calif.

[21] Appl. No.: 128,130

[22] Filed: Dec. 3, 1987

[51] Int. Cl.⁴ .............................................. H04N 7/18
[52] U.S. Cl. .................................. 358/106; 358/101; 358/107
[58] Field of Search ....................... 358/101, 106, 107; 356/394, 398

[56] References Cited

U.S. PATENT DOCUMENTS 4,347,001  8/1982  Levy ................................... 356/398
4,553,834 11/1985  Ayata .................................. 364/490
4,559,603 12/1985  Yoshikawa ........................... 356/394
4,579,455  4/1986  Levy ................................... 358/106

Primary Examiner—Howard W. Britton
Attorney, Agent, or Firm—Rosenblum, Parish & Bacigalupi

[57] ABSTRACT

A method of inspecting repeating pattern devices according to which an image of the patterns is aligned with an array of pixels in the image detection plane of an optical detector. The image is magnified to a scale so that features of patterns repeated in the image occupy corresponding pixels or groups of pixels repeated in the array. Data is resolved from selected pixels and directly compared either to data obtained from corresponding pixels or from a data base, whereby defective features are identified through well-known data comparison techniques.

14 Claims, 6 Drawing Sheets

METHOD AND APPARATUS FOR DETECTING DEFECTS IN REPEATED MICROMINIATURE PATTERNS

BACKGROUND OF THE INVENTION

1. Field of the Invention

The present invention relates generally to defect detection methods and apparatus, and more particularly to a method and apparatus for automatically detecting defects on semiconductor wafers, photomask reticles, flat panel TV screens, and other devices having repeating arrays or features forming a part thereof.

2. Discussion of the Prior Art

Previously, automatic inspection of defects on wafers and similar objects or surfaces having repeating patterns has been achieved by either comparing one die on the wafer to another die positioned on the same wafer, or by comparing the die to a reference die or to a data base. However, there are two major factors that limit the sensitivity of such defect detection processes:

1. The images of the two comparison dice are not digitized in exactly the same position relative to the image sensor. This is a result of a combination of factors including stage positioning error, spacing error, etc. Although, the offset between the two images being compared can be easily reduced to less than half of a pixel by moving the two images relative to each other within image memory, it can be shown that the residual alignment error, which can be as large as 0.5 pixel, causes artificial differences in the two comparison images and can be mistaken for a defect. To reduce false alarms due to this alignment error, defect detection sensitivity has to be reduced. On the other hand, to increase defect detection sensitivity without increasing the false alarm rate, one has to reduce the alignment error.

2. The two comparison images can have differences caused by normal process variations even though there is no defect. Semiconductor processes, like most processes, have finite tolerances. Normal process variations refer to variations that are within acceptable limits of the process. These can result in variations in line width, variations in reflectivity or contrast of the image, and variations in layer-to-layer alignment from one die to another. For example, variations of line width can be due to exposure variations of the stepper; variations in reflectivity can be due to film thickness variations in the wafer, and layer-to-layer alignment variation can be due to misalignment of the stepper or aligner. These process variations usually occur across wafers from one die to another. However, the observation has been made that within a localized area of a die, such as within one field of view of the sensor, the process remains constant and no significant variations exist.

SUMMARY OF THE PRESENT INVENTION

It is therefore a primary objective of the present invention to provide an improved method and apparatus for detecting very small defects in repeating patterns.

Another objective of the present invention is to provide a method and apparatus for automatically detecting defects on multi-patterned devices which is insensitive to normal process variations.

Still another objective of the present invention is to provide a method and apparatus which has high defect detection sensitivity but which uses relatively simple and inexpensive image processing hardware.

Briefly, in accordance with the present invention, a method of inspecting multi-patterned devices is provided wherein an image of the device is aligned relative to a pixel axis lying in the image detection plane of an optical detector, the relative size of the image relative to the detector is adjusted so that the period of the repeating pattern of the image in the detection plane has a dimension that is an integer multiple of the pixel dimension resolved by the detector so that like features appearing in the image are caused to occupy corresponding pixels or groups of pixels, and the data contained in such pixels is directly compared either to data obtained from such corresponding pixels or to information contained in a data base and defects are identified using well known data comparison techniques. An advantage of the present invention is that it provides a method that has very high sensitivity to abnormal variations and is not sensitive to normal process variations.

Another advantage of the present invention is that it is applicable to reflected light, transmitted light, fluorescent mode, and other illuminations schemes.

Still another advantage of the present invention is that it only requires simple and relatively inexpensive image processing hardware.

Yet another advantage of the present invention is that it avoids most problems associated with the inspection of multi-layered wafers; such as line-width variations, alignment variations, and reflectivity variations.

These and other objects and advantages of the present invention will no doubt become apparent to those of ordinary skill in the art after having read the following detailed description of the preferred embodiments illustrated in the several figures of the drawing.

IN THE DRAWING

DETAILED DESCRIPTION OF THE PREFERRED EMBODIMENTS

Figure 1:
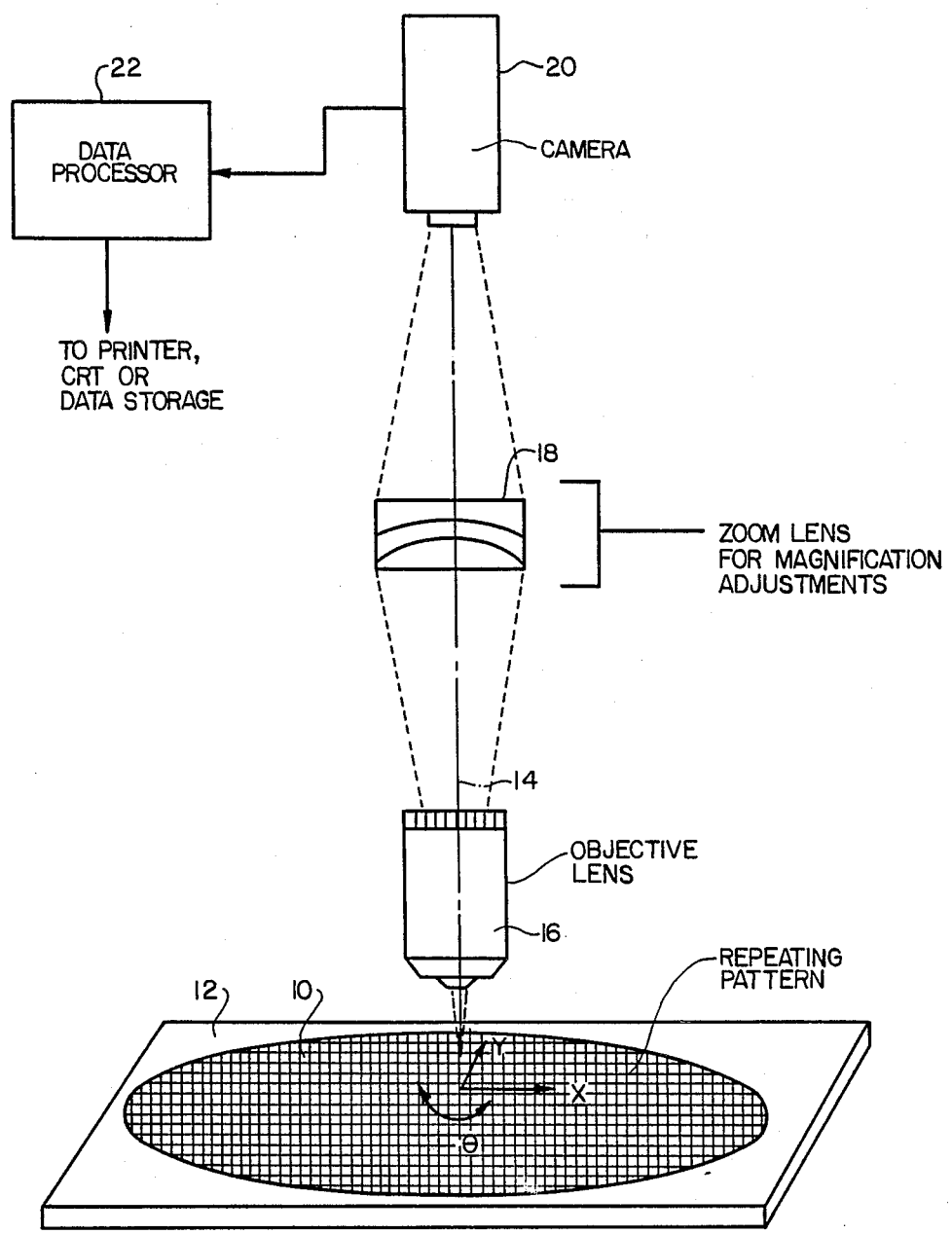
FIG. 1 is a diagram schematically illustrating a first embodiment of apparatus for implementing the present invention.

Referring now to FIG. 1 of the drawing there is shown in simplified schematic form the basic mechanical and electro-optical components required to implement the present invention. As indicated, a wafer, reticle, photomask, flat panel T.V. screen, or the like, shown at 10 is affixed to a carrying stage 12 which is either manually or electronically controllable to move the object 10 in either the X, Y or $\theta$ directions relative to an intersecting vertically disposed optical axis 14. The upper surface of object 10 is typically comprised of a multiplicity of identical patterns arranged in a regular array of orthogonal rows and columns with the content of the several patterns differing only due to process variations or defects.

Disposed along the axis 14 is an objective lens 16 for selectively focusing an image of either the whole or a particular portion of the object 10 through a zoom lens 18 and into the aperture of a camera 20. In this embodiment, camera 20 would typically be a video camera in which the screen size and image pixel definition are fixed and the size of the image input thereto is variable by adjustment of the zoom lens 18. Alternatively, camera 20 could be a CCD camera or any other similar device having the ability to resolve the data content of small discrete portions of an image. The output of camera 20 is fed into data processing electronics 22 which compare pixel data appearing in the image either to data from other portions of the image or to information contained in a data base.

Figure 2:
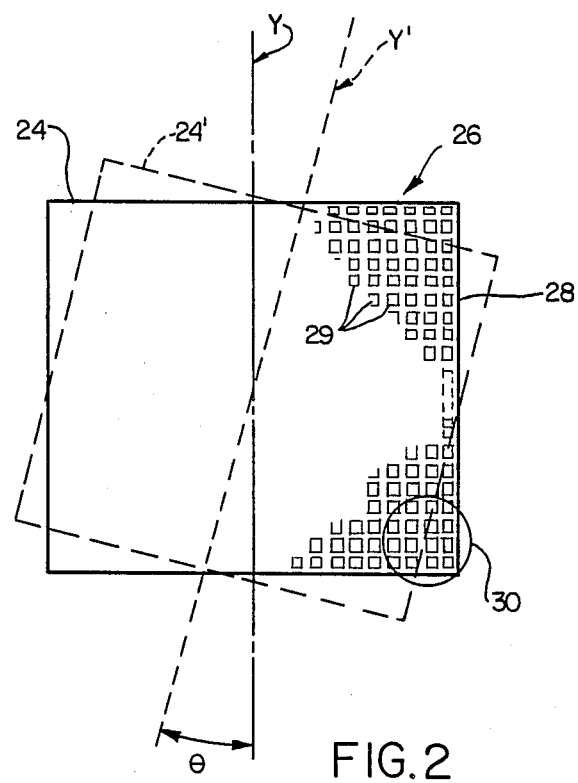
FIGS. 2–5 are diagrams schematically illustrating operation of the present invention.

To illustrate the method of the present invention, reference is made first to FIG. 2 wherein the detector surface of camera 20 is depicted by the area inside rectangle 24 and the optical aperture of camera 20 is represented by the area inside circle 26. The image 28 of a portion of the patterns contained on object 10 is shown by the array of patterns 29.

In accordance with the present invention, the image 28 is first projected at a low magnification onto the sensitive face 24 of camera 20 and a determination is made as to whether or not the rows and columns appearing in the image 28 are aligned with the Y axis of the detector surface. If not, and the relative orientation is as indicated by the dashed lines 24', then the object is rotated through the angle $\theta$ so that the Y axis is aligned with the vertical columns of patterns in the image 28. Numerous well known techniques can be used to determine when the image is aligned with a particular axis of the camera.

Figure 3:
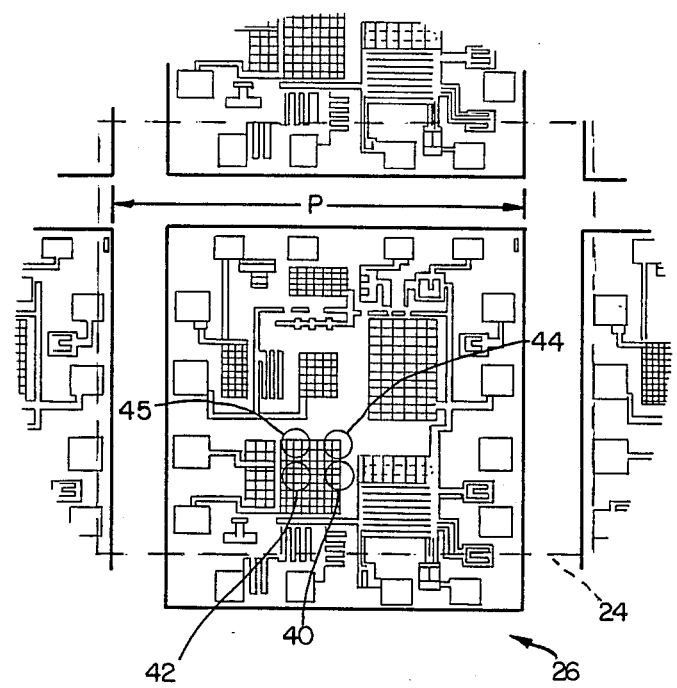

Once the image is properly aligned, the next step is to increase the magnification of zoom lens 18 until an image approximately corresponding to the size of a single die or a selected portion thereof having repeated features is caused to fill the aperture 26 of the camera 20, as depicted in FIG. 3. At this point the zoom is further adjusted until the period or pitch "P" of the repeating pattern in the image is equal to the dimension of an integral number of detection pixels.

Having now rotated the image into alignment with the camera, and having adjusted the magnification such that the pitch of the repeating pattern of the image cast upon the sensitive surface of the camera 20 is a predetermined integer number of pixels, it will be appreciated that insofar as the presently viewed image is concerned, process variation is no longer significant and similar features of the image can be directly compared on a pixel by pixel basis. More specifically, in order to perform an inspection of any feature of the pattern, the pixel or pixels containing the subject pattern are compared to any other pixel or group of pixels containing the same feature, and if there is a material variance between the two, then a defect has been detected. For example, one can compare the feature encircled at 40 in FIG. 3 to the corresponding feature encircled at 42 or 45, or can compare the feature shown at 40 to the feature at 45. For convenience however, most comparisons are made between corresponding features disposed along common horizontal or vertical lines.

Figure 4:
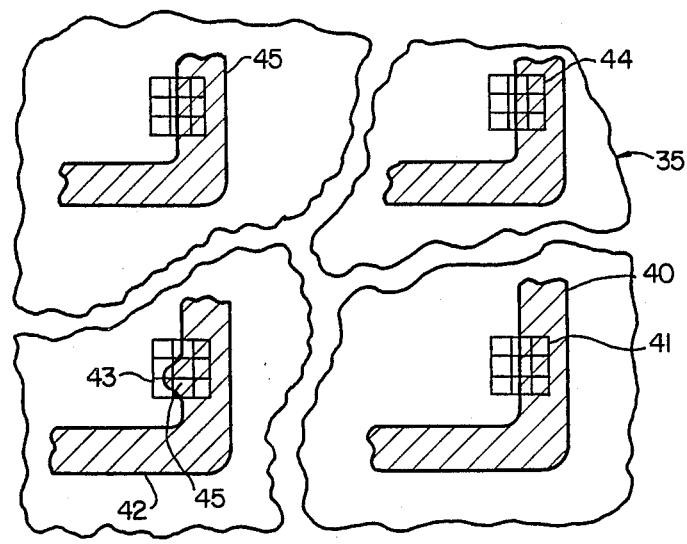

In FIG. 4, the features 40, 42, 44 and 45 are magnified and overlayed by a pixel grid 35. A simple comparison of pixel data taken from pixels corresponding to the same type of feature used in other parts of the pattern will indicate whether or not one of the compared features is different and thus defective. For example, if the data contained in a particular pixel, or in the 3×3 array of pixels 41 covering a portion of the feature 40, were to be compared to a corresponding pixel, or the corresponding set of pixels 43 covering the feature 42, it is apparent that the detected difference therebetween would evidence the presence of the defect 45.

Figure 5:
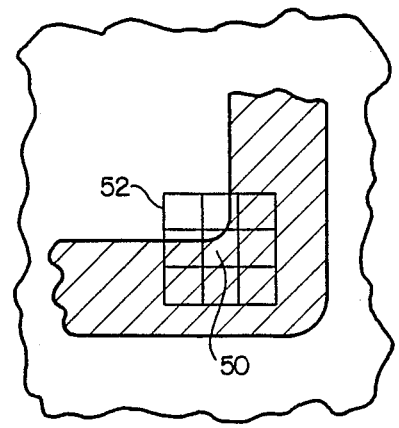

Similarly, as depicted in FIG. 5, the information contained in a single pixel 50 or group of pixels 52 can be compared to corresponding information contained in a data base.

Figure 6:
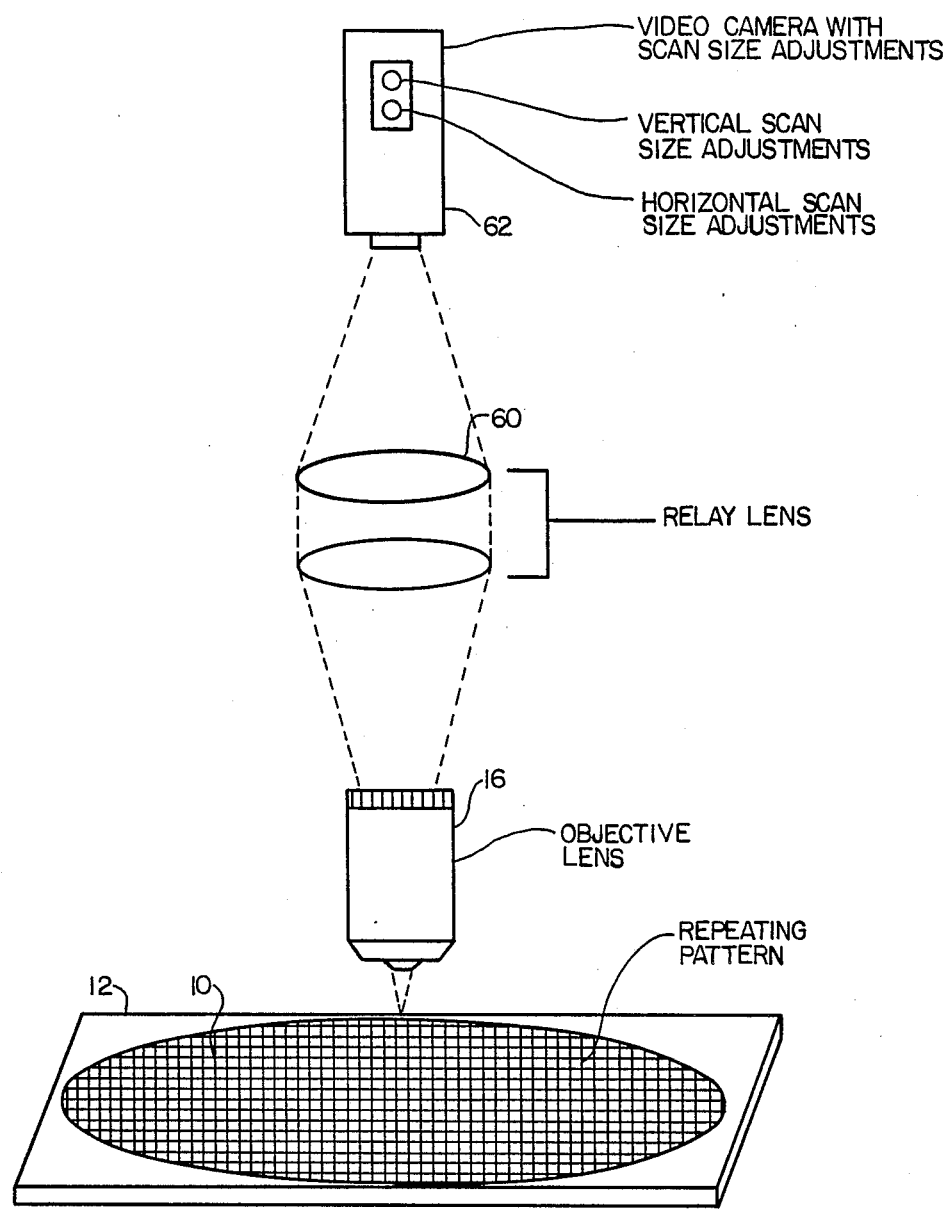
FIGS. 6–8 illustrate alternative embodiments of apparatus for implementing the present invention.

Referring now to FIG. 6, an alternative implementation of the present invention is depicted wherein instead of using a zoom lens to provide adjustment of the image size relative to the detector size, a simple relay lens 60 is used in combination with the objective lens 16 and a video camera 62 having vertical scan size adjustment and horizontal scan size adjustment capability. In this implementation, instead of varying the image size in order to make the image pattern period P an integral multiple of detector pixels, the size of the effective area of the detector portion of the video screen is in effect varied. As in the previously described embodiment, the detector size adjustment is made following alignment of the patterned image with either the vertical or horizontal axis of the effective detector surface.

Figure 7:
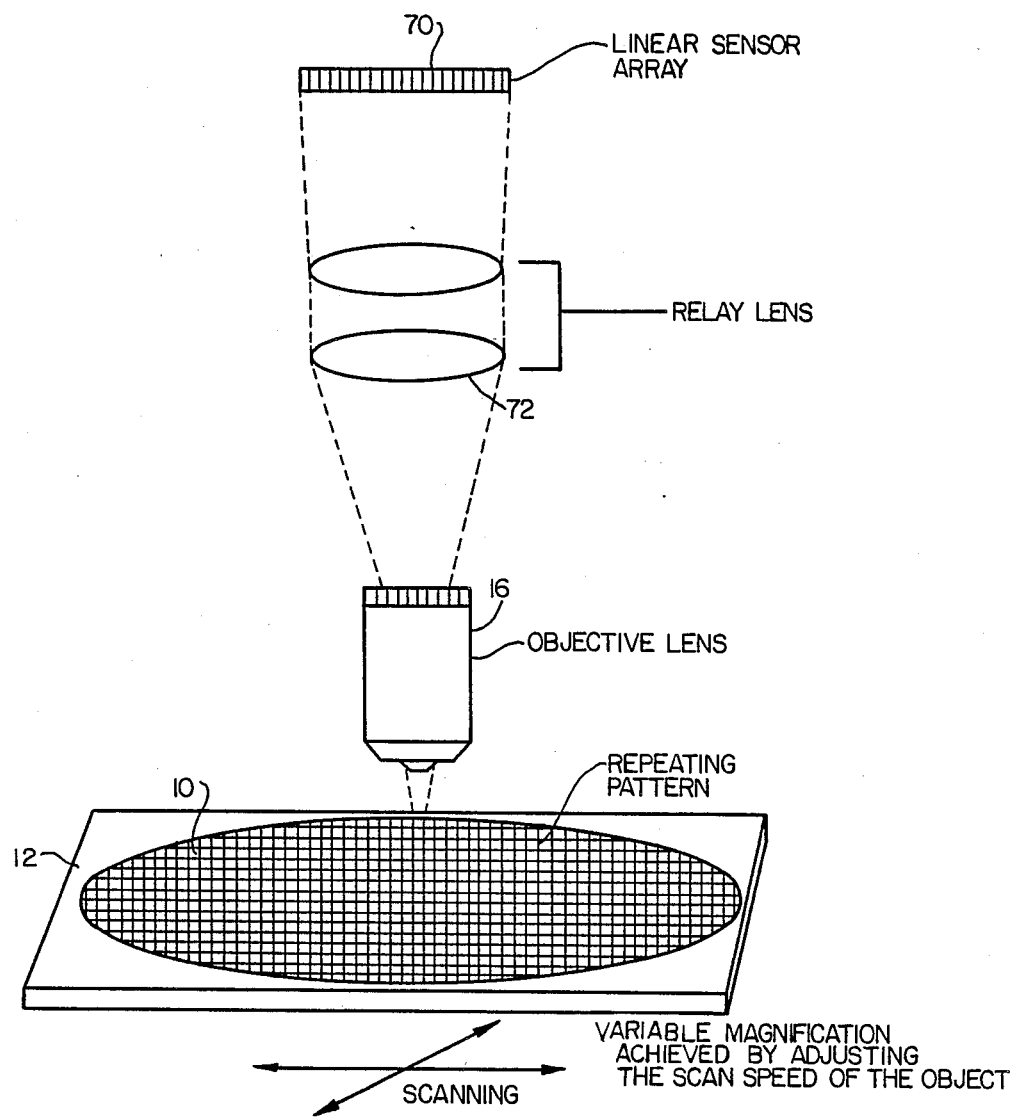

In FIG. 7 another alternative apparatus for implementing the present invention includes the use of a linear sensor array 70 comprised of, for example, a 512×1 detection means positioned to receive the image projected thereupon by an objective lens 16 through suitable relay lens 72. In this case, scanning is accomplished by moving the stage 12 carrying the object 10 in a scanning direction normal to the length of the sensor array. The effective sizing of the pixels and thus the adjustment of period dimensions is accomplished by adjusting the scan speed of the stage relative to the sample rate of the detector. It will be appreciated that in using this implementation substantially the same result will be obtained.

Figure 8:
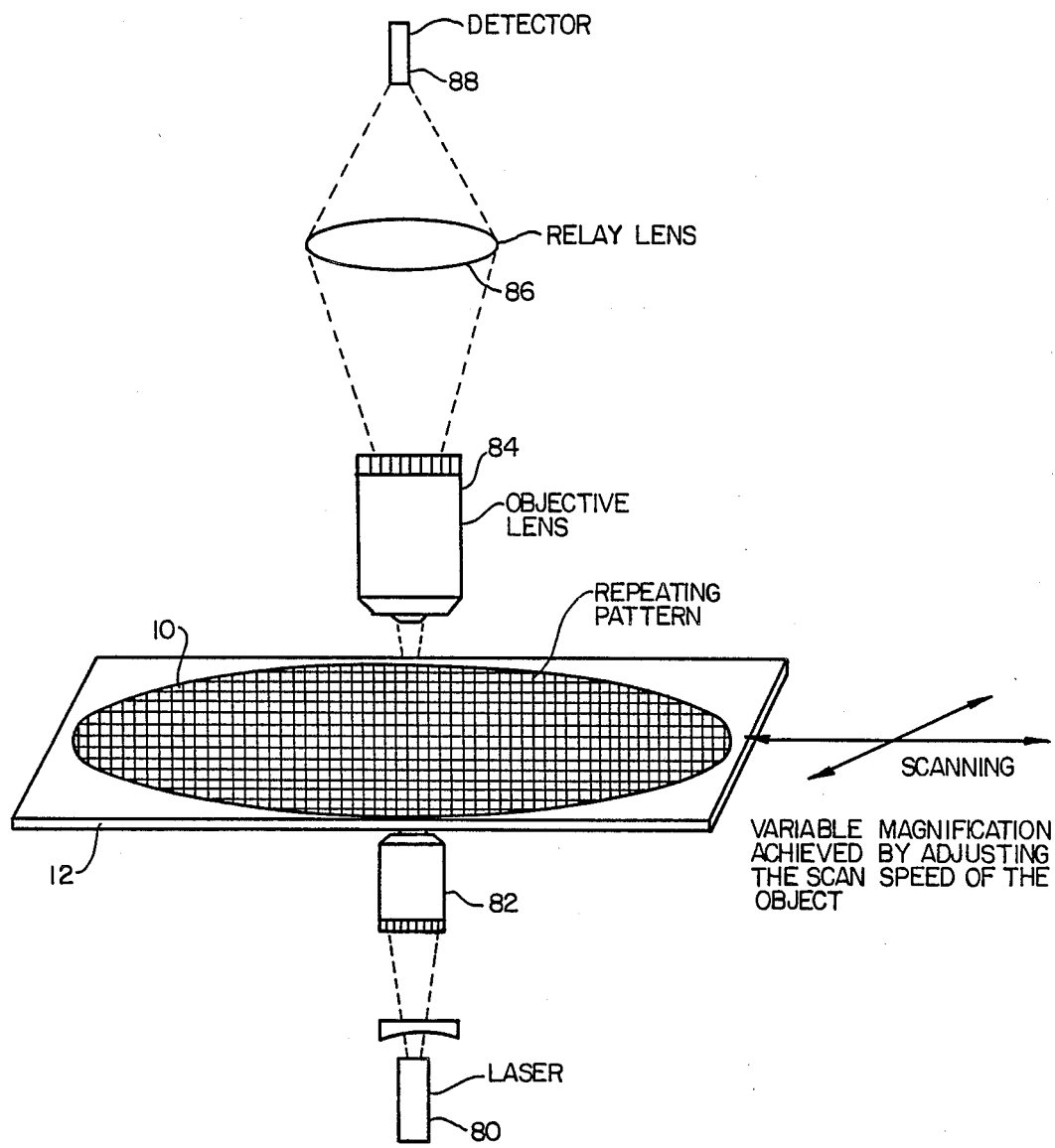

Turning now to FIG. 8 of the drawing, still another alternative embodiment of apparatus for implementing the invention is depicted wherein the scanning operation is accomplished by means of a laser imaging system including a laser 80, appropriate focusing lens 82, a stage 12 for carrying the object 10, an objective lens 84, a relay lens 86, and a detector 88. In accordance with this implementation, which may be either a back-lit scanning embodiment or a front-lit scanning embodiment, variable magnification is achieved by adjusting the scanning speed of the laser scanning system.

In summary, the method of the present invention is comprised of essentially the following steps:

1. Providing an image detection means capable of resolving the information content of each pixel of an array of m×n pixels of a light image projected thereupon;

2. Illuminating an object having illuminatable feature determining patterns repeated in regular array over a surface area thereof;

3. Projecting a focused image of light from the object onto the detection means;

4. Rotating the object relative to the detection means so that an axis of the image is aligned with an axis of the detection means;

5. Adjusting the magnification of the image such that the dimension of the period of said repeated patterns in the image is equivalent to the distance across a selected integer number of pixels of said m×n array; and 6. Comparing one repeated feature to another (or to a data base) to detect defects.

Having thus described the present invention in terms of several preferred forms of implementation, it is understood that various other alternatives as well as alterations and modifications thereof will become apparent to those skilled in the art. It is therefore intended that the following claims be interpreted as covering all such alternatives, alterations and modifications as fall within the true spirit and scope of the invention.

We claim:

1. A method of detecting defects in microminiature patterns repeated over a particular surface area of an object such as a semiconductor wafer, photomask, reticle or flat panel TV screen, comprising the steps of:

providing an image detection means capable of resolving the information content of each pixel of an array of m×n pixels of a light image projected thereupon;

illuminating an object having illuminatable feature determining patterns repeated in a regular array over a surface area thereof;

projecting a focused image of light reflected from said surface area onto said detection means;

rotating said object relative to said detection means so that an axis of said image is aligned with an axis of said detection means;

adjusting the magnification of said image such that the dimension of the period of said repeated patterns in said image is equivalent to the distance across a selected integer number of pixels of said m×n array; and comparing one repeated feature to another to detect said defects.

2. A method of detecting defects as recited in claim 1 wherein said image detection means is a video camera, and magnification adjustment is accomplished by varying the vertical and horizontal scan size of said video camera.

3. A method of detecting defects as recited in claim 1 wherein said image detection means is a linear sensor array forming a part of a linear sensor scanning system, and said magnification is accomplished by varying the scan speed of said system.

4. A method of detecting defects as recited in claim 1 wherein said detection means includes a scanning laser system, and said magnification is accomplished by varying the scanning rate thereof.

5. A method of detecting defects as recited in claim 1 wherein a zoom lens means is used to adjust the size of the image projected onto said image detection means.

6. A method of detecting defects as recited in claim 5 wherein said image detection means is a CCD camera means.

7. A method of detecting defects as recited in claim 5 wherein said image detection means is a video camera means having a fixed scan size.

8. A method of detecting defects in microscopic features in patterns repeated across a given surface area of an object such as a semiconductor wafer, photomask, reticle or flat panel TV screen, comprising the steps of:

providing an image detection means having a field of view with an array of m×n pixels capable of resolving the information content of a light image projected onto said field;

illuminating an object surface area on which an array of regularly repeated patterns display illuminatable features;

focussing light from said surface area into an image projected onto said field of view of said detection means;

using said image detection means to detect said image;

repositioning said object surface relative to said detection means to align a selected axis of said image with a selected axis of said array of pixels;

magnifying said image to scale the pitch of said patterns to correspond to the width of a selected number of pixels;

resolving, with said detection means, the information content of selected pixels; and comparing one said feature in one pattern to another in another pattern to identify defects in said one feature.

9. A method as recited in claim 8 wherein said image detection means comprises a video camera, and said step of magnifying to scale varies the size of the field of view of said camera.

10. A method as recited in claim 8 wherein said image detection means comprises a linear sensor array in a linear sensor scanning system, and wherein said step of magnifying to scale varies the scanning speed of said system.

11. A method as recited in claim 8 wherein said detection means comprises a scanning laser system, and said step of magnifying to scale varies the scanning rate of said system.

12. A method as recited in claim 8 wherein said step of magnifying uses a zoom lens to scale said pitch.

13. A method as recited in claim 12 wherein said image detection means comprises CCD camera means.

14. A method as recited in claim 12 wherein said image detection means comprises a video camera having a fixed size field of view.

* * * * *